United States Patent [19]
Van Ness

[11] Patent Number: 5,788,063
[45] Date of Patent: Aug. 4, 1998

[54] SUTURE ANCHOR PACKAGE

[75] Inventor: William Van Ness, Flemington, N.J.

[73] Assignee: Ethicon, Inc., Somerville, N.J.

[21] Appl. No.: 924,428

[22] Filed: Aug. 27, 1997

Related U.S. Application Data

[63] Continuation of Ser. No. 631,718, Apr. 10, 1996, abandoned.
[51] Int. Cl.$^6$ ............................................ A61B 17/06
[52] U.S. Cl. .......................... 206/63.3; 206/486; 206/380
[58] Field of Search .................................. 206/438, 63.3, 206/380, 227, 486

[56] References Cited

U.S. PATENT DOCUMENTS

| | | | |
|---|---|---|---|
| 4,023,678 | 5/1977 | Fiedler | 206/438 |
| 4,615,435 | 10/1986 | Alpern et al. | 206/63.3 |
| 4,828,108 | 5/1989 | Roth et al. | 206/486 |
| 4,884,681 | 12/1989 | Roshdy et al. | 206/63.3 |
| 5,358,624 | 10/1994 | Roshdy et al. | 206/63.3 |
| 5,425,445 | 6/1995 | Brown et al. | 206/380 |
| 5,460,263 | 10/1995 | Brown et al. | 206/380 |
| 5,487,469 | 1/1996 | Roshdy et al. | 206/63.3 |

*Primary Examiner*—Paul T. Sewell
*Assistant Examiner*—Nhan T. Lam
*Attorney, Agent, or Firm*—Emil Richard Skula

[57] ABSTRACT

A folder package for a suture anchor. The package has a base panel foldably connected to a connecting panel. A cover panel is foldably connected to the connecting panel. First and second end connecting panels are foldably connected to the cover panel. A needle park member is mounted to the base panel to retain surgical needles and optionally retain the suture anchor. A handle cover panel having opposed sides is foldably connected to the base panel. A connecting panel having opposed major and opposed minor sides is foldably connected along a first major side to an opposite side of the handle cover panel, and a tab member is foldably connected to the second major side of the connecting panel. The base panel has a tab member formed by a U-shaped slit for retaining the needle park member. The base panel also has L-shaped slits forming L-shaped members for retaining a shaft of a suture anchor applicator. The base panel further has a pair of tab member formed form U-shaped slits and tabs to retain a handle of a suture anchor applicator. The cover panel has a plurality of tabs and tab pockets, formed by arcuate slits, for locking the package by engaging a side of the base panel in the tab pockets. A portion of each end panel is also engaged in a tab pocket to further provide for the locking of the package.

3 Claims, 7 Drawing Sheets

SUTURE ANCHOR PACKAGE

This is a continuation of application Ser. No. 08/631,718, filed Apr. 10, 1996, abandoned.

TECHNICAL FIELD

The field of art to which this invention relates is packaging, in particular, packages for suture anchors.

BACKGROUND OF THE INVENTION

Folder packages for surgical sutures and surgical needles are well known in the art. Similarly, folder packages for suture anchors are also known. Suture anchors are medical devices which are used in orthopedic surgical procedures to attach soft tissue such as tendons or ligaments to bone. Surgical sutures are typically attached to the suture anchors, and, surgical needles are typically mounted to the ends of sutures. Once an anchor is mounted in bone, the surgical sutures and needles are used by the surgeon to attach the soft tissue to the surface of the bone.

A package for a suture anchor must protect a suture anchor, applicator, sutures and needles during shipping, storage, sterilization procedures, and the like. The package must also prevent the suture anchor, applicator, sutures and needles from shifting in the package during shipping and storage. The suture anchor, applicator, sutures and needles must be easily removed from the package at the hospital during surgery.

There is a constant need in this art for improved packages for suture anchors which protect the suture anchors, and associated applicators, sutures and needles, and which prevents them from shifting during shipping and handling. Such improved packages will also allow the suture anchors, and associated applicators, needles and sutures, to be readily removed from the packages without any binding or hang-ups.

DISCLOSURE OF THE INVENTION

Therefore, it is an object of the present invention to provide an improved folder package for suture anchors.

Accordingly, a folder package for a suture anchor is disclosed. The package has a base panel, said base panel having opposed first and second major sides and opposed first and second minor sides. A connecting panel having opposed first and second major sides and opposed first and second minor sides is foldably connected along a first major side to a first major side of the base panel. A cover panel having a first and second opposed major sides and first and second opposed minor sides is foldably connected along a first major side to the second side of the major side of the connecting panel. A first end connecting panel is foldably connected to a first minor side of the cover panel. A second end connecting panel is foldably connected to the other minor side of the connecting panel. A first end panel is foldably connected to the first end connecting panel. A second end panel is foldably connected to the second end connecting panel. A needle park member is mounted to the base panel to retain surgical needles and optionally retain the suture anchor. A handle cover panel having opposed sides is foldably connected along one side to a second major side of the base panel. A connecting panel having opposed major and opposed minor sides is foldably connected along a first major side to an opposite side of the handle cover panel, and a tab member is foldably connected to the second major side of the connecting panel. The base panel has a tab member formed by a U-shaped slit for retaining the needle park member. The base panel also has L-shaped slits forming L-shaped members for retaining a shaft of a suture anchor applicator. The base panel further has a pair of tab members formed from U-shaped slits to retain a handle of a suture anchor applicator. The cover panel has a plurality of tabs and tab pockets, for locking the package, formed by arcuate slits, for locking the package by engaging a side of the base panel in the tab pockets. A portion of each end panel is also engaged in a tab pocket to lock the package.

These and other features and advantages of the invention will become more apparent from the following description and accompanying drawings.

BEST MODE FOR CARRYING OUT THE INVENTION

Figure 1:
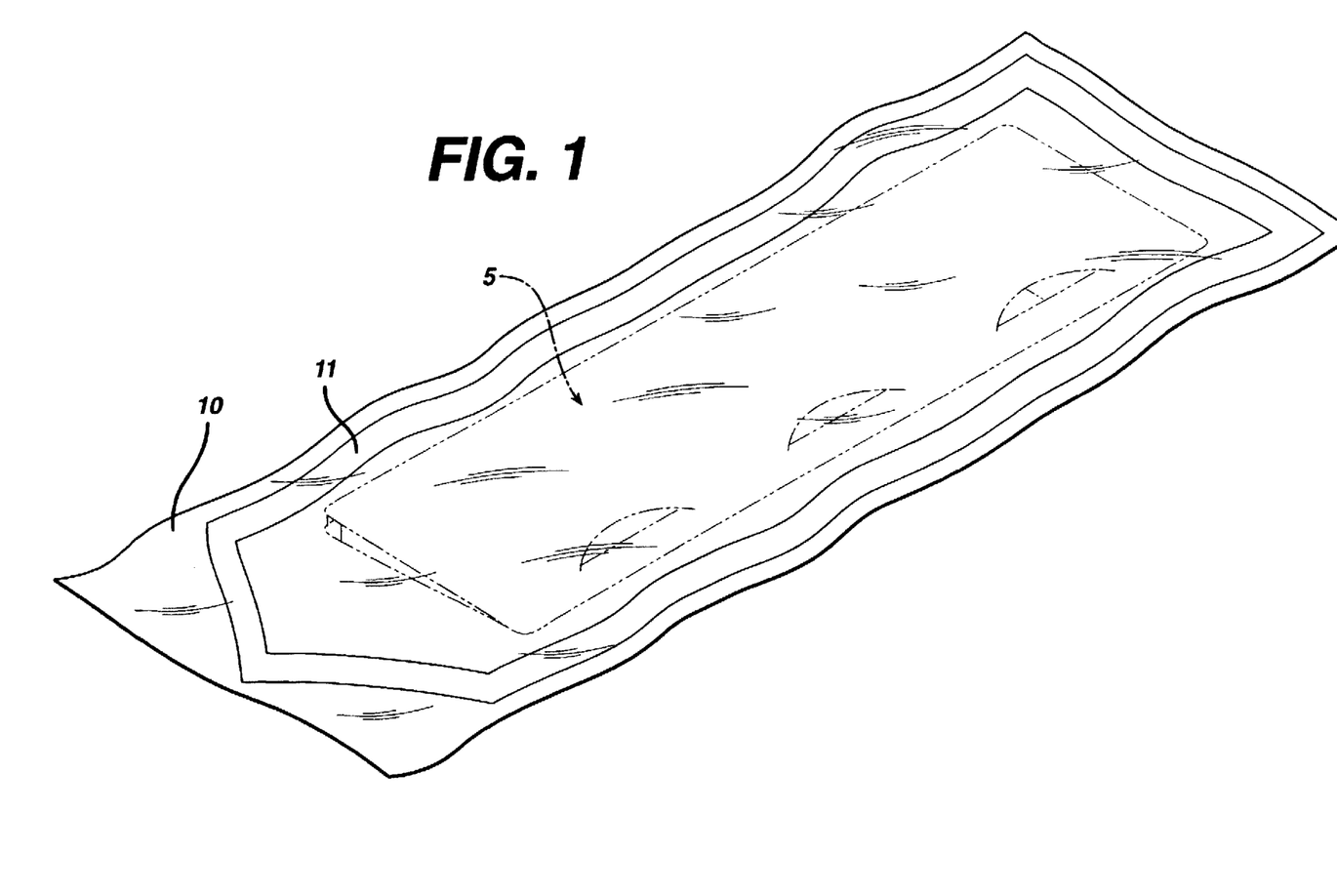
FIG. 1 is a perspective view of a suture anchor package of the present invention contained in an outer sealed pouch.

A perspective view of the package 5 of the present invention is seen in FIG. 1. Package 5 is seen to be fully assembled and contained within a sealed outer envelope 10 having seal 11. Outer envelope 10 is preferably a conventional moisture-proof pouch useful for sterilized moisture-sensitive medical devices, e.g., bioabsorbable devices made from bioabsorbable polymers such as sutures, tissue tacks, suture anchors, implants, etc.

Figure 2:
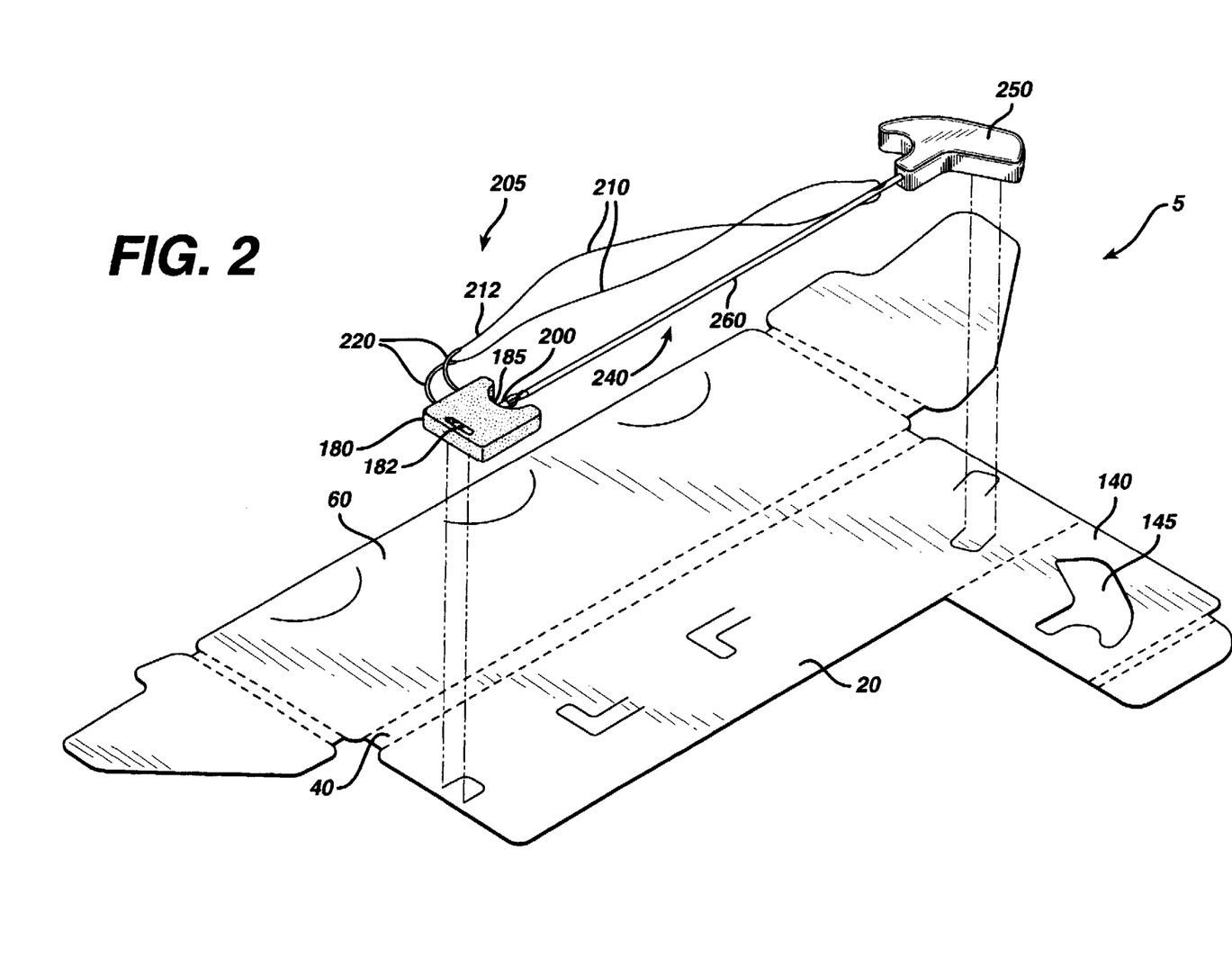
FIG. 2 is a perspective view of an unassembled package of the present invention and a suture anchor assembly and suture anchor applicator.
Figure 3:
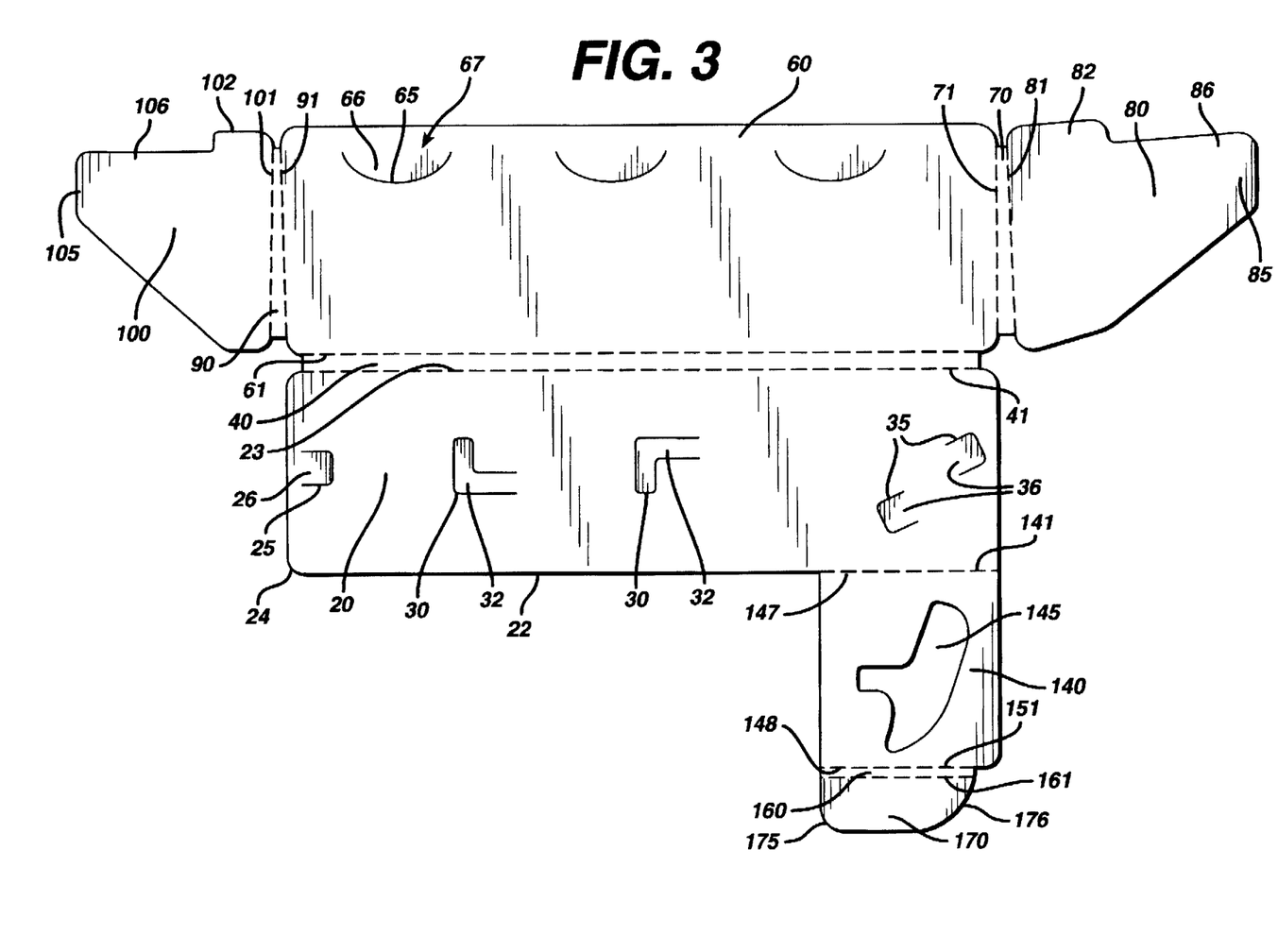
FIG. 3 is a plan view of a suture anchor package of the present invention prior to loading the suture anchor assembly and applicator, and prior to folding and assembling the package.

Referring now to FIGS. 1–3, a top view of the package 5 of the present invention is seen prior to folding and assembly. The package 5 is seen to have a substantially rectangular base panel 20 having a pair of opposed major sides 22 and 23 and a pair of opposed minor sides. Base panel 20 is seen to have radiused corners 24. Foldably connected to the second major side 23 of the base panel 20 along fold line 41 is the connecting panel 40. Connecting panel 40 is seen to be a substantially rectangularly shaped member having a pair of opposed major sides and a pair opposed minor sides. Foldably connected to the connecting panel 40 along fold line 61 is the cover panel 60. The closure panel 60 is seen to be a substantially rectangularly shaped panel having a pair of opposed major sides and a pair of opposed minor sides. The closure panel 60 is seen to have radiused corners 62. Contained in the closure panel 60 are the slots 65 forming tabs 66 and tab pockets 67. Foldably connected to each minor side end of the closure panel 60 are the optional end connecting panels. First end connecting panel 70 is seen to have a substantially trapezoidal shape with opposed major and minor sides and is connected along fold line 71 to the cover panel 60. First end panel 80 is seen to have an irregular shape. The end panel 80 is connected along fold line 81 to a major side of connecting panel 70. First end panel 80 is seen to have tab projection 82 and end 85. End 85 has engagement section 86. Second end connecting panel 90 is seen to have a substantially trapezoidal shape with opposed major and minor sides and is further seen to be foldably connected to the other minor end of the closure panel 60 along fold line 91. Foldably connected to a major side of the second end connecting panel 90 along fold line 101 is the second end panel 100. Second end panel 100 is seen to have tab member 102 extending therefrom and end 105 having engagement section 106.

The base panel 20 is seen to have U-shaped slit 25 which forms tab member 26. The base panel 20 is also seen to have L-shaped slits 30 forming L-shaped tab members 32. The base panel 20 is also has a pair of opposed U-shaped slits 35 forming applicator handle retaining tabs 36. Foldably connected along a first side 147 to the first major side 22 of the base panel 20, along fold line 141, is the handle cover panel 140. Handle cover panel 140 is a substantially square shaped panel having two pairs of opposed sides. Handle cover panel 140 is seen to have irregularly shaped cut-out 145 corresponding to the shape of handle 250 of suture anchor applicator 240. Foldably connected to an opposed side 148 of handle panel 140 along fold line 151 is the connecting panel 160. Connecting panel 160 is seen to be a substantially rectangularly shaped panel having a pair of opposed major sides and a pair of opposed minor sides. Foldably connected to the other major side of the connecting panel 160 along fold line 161 is the tab panel 170. Tab panel 170 is seen to have radiused corners 175 and 176.

The suture park 180 is seen to be a substantially square shaped member having a slot 182 for receiving tab 26. If desired, the park 180 may also have a semi-circular cut-out section 185 for protecting the suture anchor 200. Although, in the presently described embodiment, suture park 180 is mechanically mounted to base panel 20 using tab member 26, other conventional mounting methods may be used including adhesives, mechanical fasteners such as staples or rivets, etc. The park 180 is preferably constructed from a conventional polymeric foam. The park 180 will be of sufficient size and shape to effectively retain and protect a suture anchor and surgical needles. If one were willing to accept any disadvantages which may be attendant, if any, park 180 may be replaced by paper members, plastic molded members, equivalents thereof and the like.

It will also be appreciated by those skilled in the art that various geometric shapes can be effectively used for the park 180 including rectangles, triangles squares, circles, etc. It will also be appreciated by those skilled in the art that the locking means used to secure the package 5 may include any conventional means in addition to tabs and tab pockets, including mechanical fasteners, rivets, adhesives and the like, if one were willing to accept any attendant disadvantages, if any. It will be appreciated by those skilled in the art that the size of the package 5 and the panels will vary in accordance with the size of the suture anchor assembly and applicator. The package 5 and the panels will be of sufficient size to effectively contain a particular suture anchor assembly and applicator as illustrated and described herein.

Figure 4:
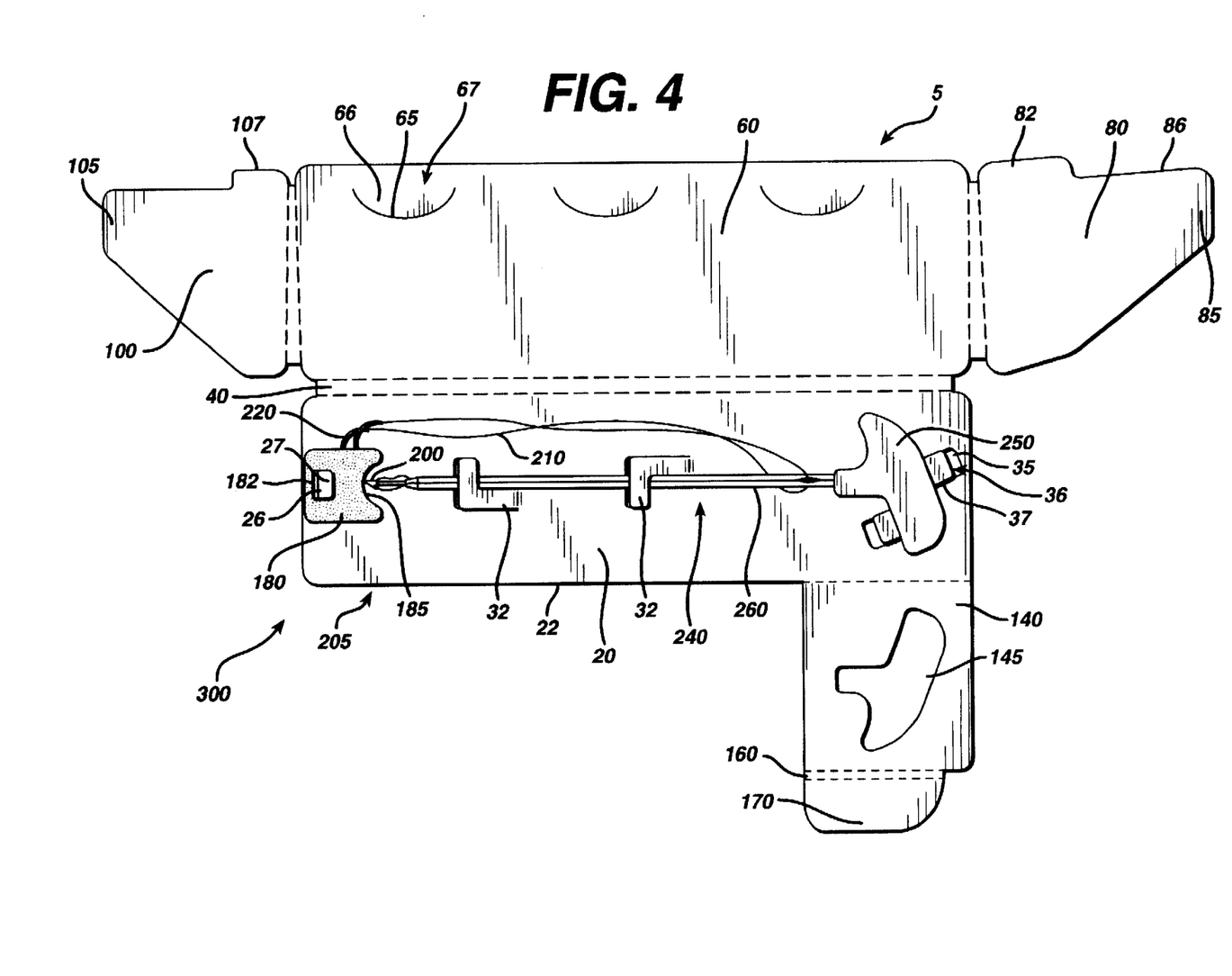
FIG. 4 is a perspective view of a package of the present invention wherein a suture anchor assembly and applicator have been mounted to the base panel of the package.
Figure 5:
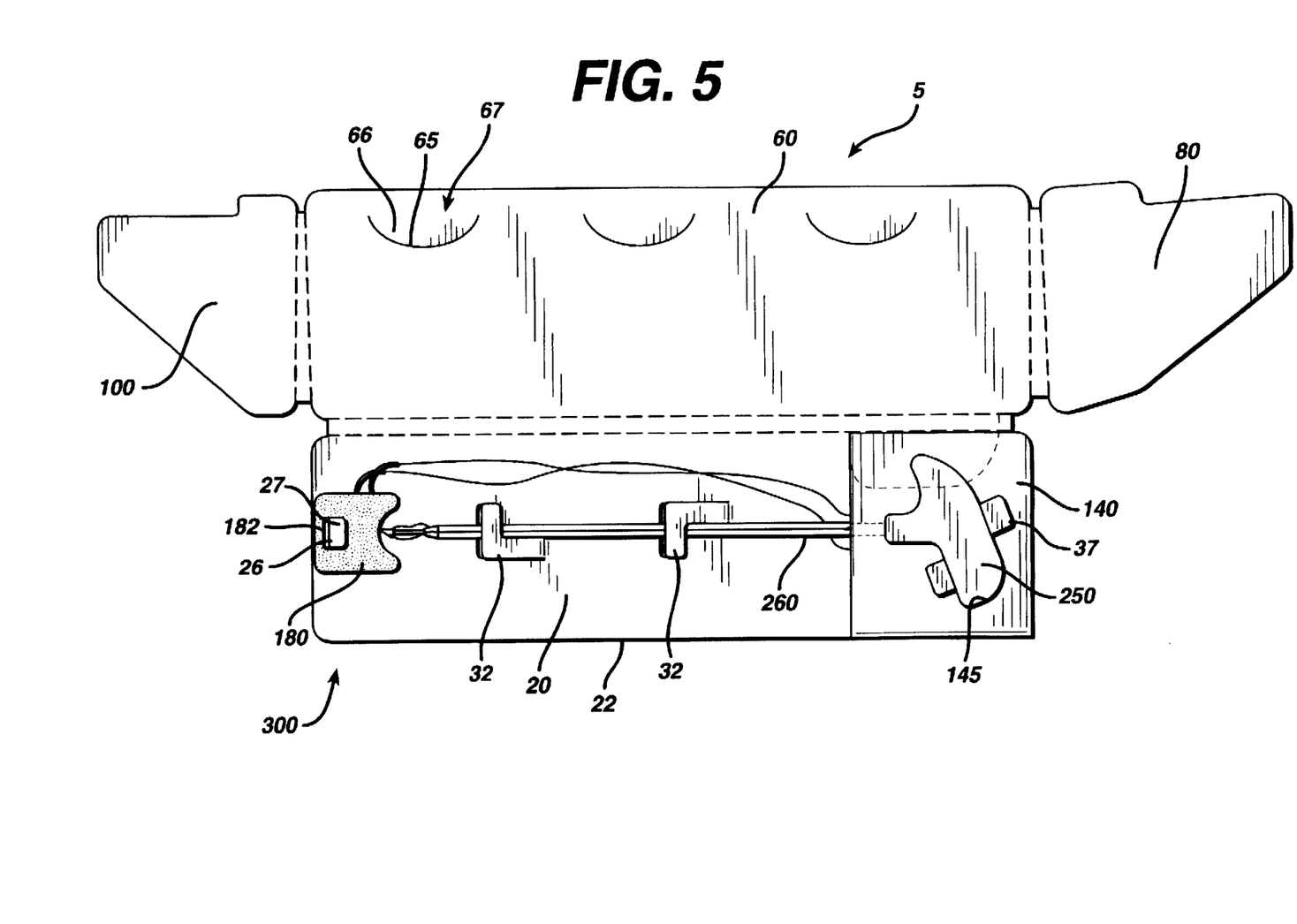
FIG. 5 illustrates the suture anchor assembly and suture anchor applicator mounted to the base panel of the package of the present invention with the handle cover panel fold over the handle.
Figure 6:
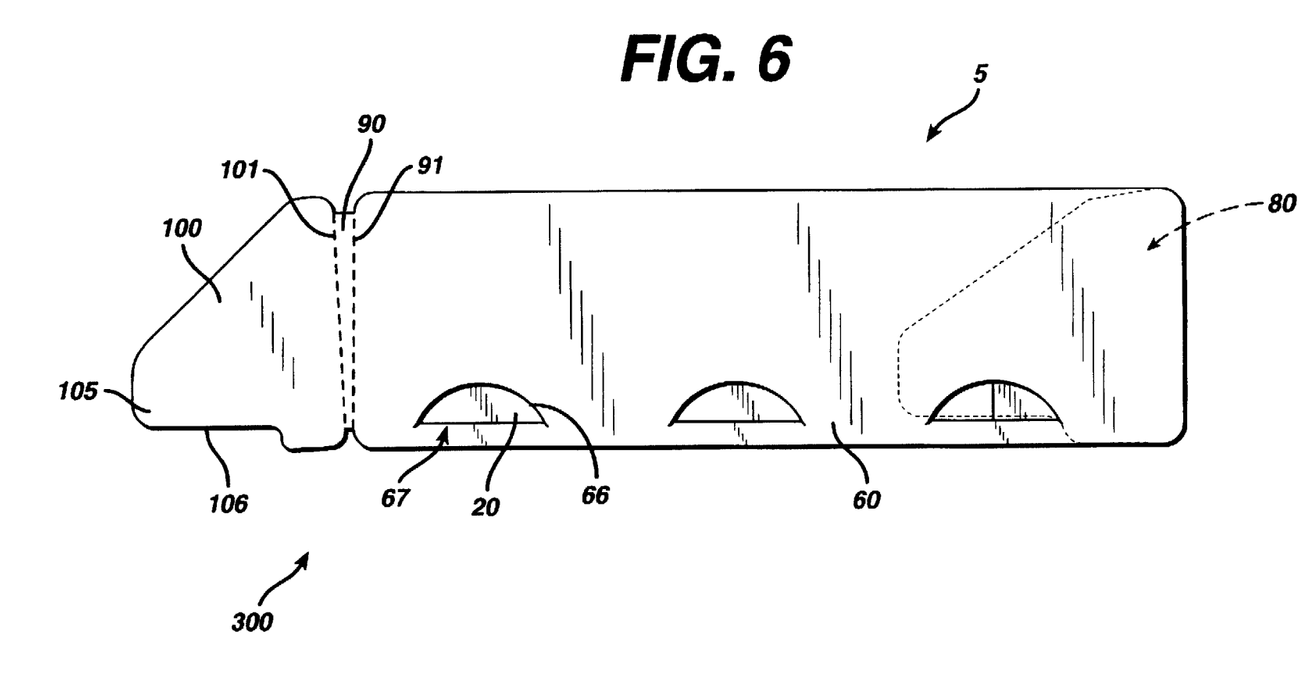
FIG. 6 illustrates the package of the present invention with the cover panel folded over and locked to the base panel and with one end panel folded over and secured in a tab pocket.

As seen in FIG. 2 and FIG. 4, a suture anchor 200 is mounted to the shaft of a suture anchor applicator 240 having handle 250 and shaft 260. The suture anchor 200 is seen to have a wedge shape, however the suture anchor 200 may have any conventional shape. Wedge shaped suture anchors are disclosed in commonly assigned, co-pending U. S. patent application Ser. No. 08/235,737 which is incorporated by reference. The suture anchor also has surgical sutures 210 mounted thereto having ends 212. Mounted to the ends 212 of sutures 210 are the conventional surgical needles 220. The suture anchor 200, sutures 210 and needles 220 form suture anchor assembly 205.

Conventional envelopes useful as outer envelope 10 may be made from polymer films including TYVEK®, polyester copolymers, polypropylene copolymers, combinations thereof, and the like. The envelopes 10 may also be made from polymer film, paper, and foil combinations. The package 5 is preferably packaged in a conventional moisture proof foil envelope 10, such as a foil envelope, when used for bioabsorbable suture anchors and sutures.

Referring now to FIGS. 4–7, the assembly of the package 5 of the present invention is illustrated. References to clockwise and counter-clockwise directions of rotation of panel are referenced to the directional arrow 300. The first step in the assembly of the suture anchor package 5 of the present invention is to mount the suture park 180 to the base panel 20 such that the tab 26 extends through slot 182 and retains the park 180 to the base panel 20 by bending the end 27 of the tab 26 which extends through slot 182 onto the top of the park 180. Then the points of needles 220 are inserted into the park 180 and the suture anchor assembly 205 and applicator 240 are laid upon the base panel 20 such that the shaft 260 of the introducer 240 is retained by the L-shaped members 32 which are folded upward about shaft 260. The handle 250 is retained by the handle retaining tab members 36 which are also folded upward. The suture anchor assembly 205 is positioned such that anchor 200 is within cut-out section 185 of park 180. Next, the handle cover panel 140 is rotated upward in a counter-clockwise manner about fold line 141 such that the handle 250 of the suture anchor introducer 240 is engaged within the opening 145 along with tab members 36; the ends 37 of tab members 36 are optionally folded downward onto panel 140. Next, the connecting panel 160 is folded down in a counter-clockwise manner about fold line 151 such that it is perpendicular to the handle cover panel 140. Then, the tab panel 170 is folded counter-clockwise about fold line 161 so that it is perpendicular to the connecting panel 160. Preferably panels 160 and 170 are folded prior to folding panel 140 onto handle 250. Tab panel 170 is placed onto the base panel 20 and underneath the handle 220. Next, the connecting panel 40 is folded in a clockwise manner about fold line 41 such that it is perpendicular to the base panel 20. Next, the cover panel 60 is folded about fold line 61 in a clockwise manner such that it covers the base panel 20 and the suture anchor assembly 205 and the applicator 240 and the handle cover panel 140. Next, the cover panel 60 is locked to side 22 of the base panel in tab pockets 67 of cover panel 60. Then, first and second end connecting panels 70 and 90 are folded, counter-clockwise and clockwise respectively, about fold lines 71 and 91 such that they are substantially perpendicular to the cover panel 60. Then, end panels 80 and 100 are folded about fold lines 81 and 101, clockwise and counter-clockwise respectively, such that the end panels are on top of the bottom of base panel 20 and tab ends 85 and 105, respectively, are each locked in a tab pocket 67 along sections 86 and 106, respectively. The package 5 is then fully assembled and is then inserted into an outer envelope 10 and sealed prior to sterilization.

Figure 7:
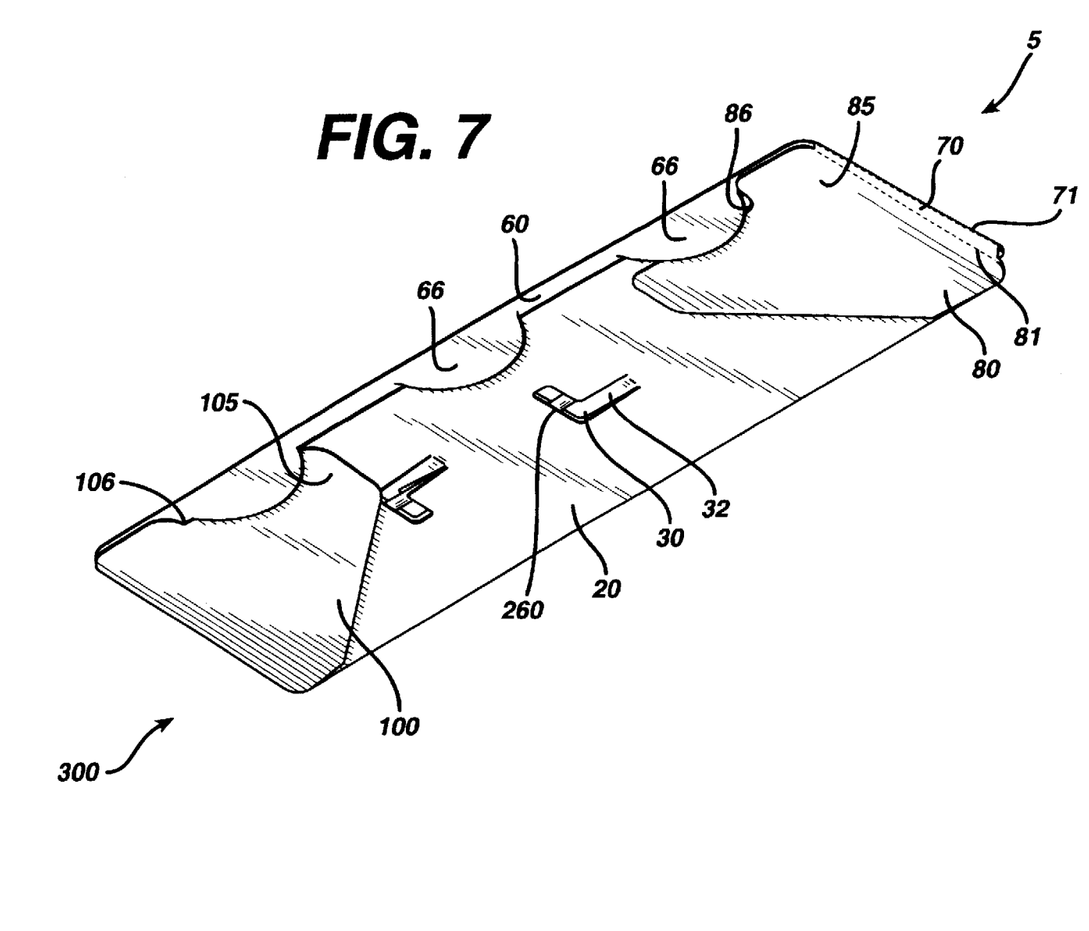
FIG. 7 is a bottom perspective view illustrating the package of the present invention fully assembled with both end panels secured in tab pockets.

In order to remove suture anchor assembly 205 and applicator 240 from the package 5 of the present invention, the first step is for the operating room professional to remove the package 5 from the pouch 10 by tearing the pouch 10 apart. The package 5 is then typically placed in a sterile field. Then the first and second end panels 100 and 80 are unlocked from the tab pockets 67 by pulling the ends 105 and 85 respectively such that the sides 86 and 106 are disengaged from the tab pockets 67. Then the side 22 of the base panel 20 is disengaged from the tab pockets 67 and the cover panel is rotated about fold line 61.

Then the handle cover panel 140 is rotated upwardly about fold line 141 away from the handle 250 and the handle 250 and shaft 260 are grasped and removed from the L-shaped members 32 and the tabs 36 and the needles 220 and anchor 200 are removed from the suture park 180.

The packaged medical devices of the present invention are typically sterilized using conventional sterilization equipment and processes. Examples of the sterilization processes which can be used on the bioabsorbable suture anchors and sutures packaged in the fordable packages 5 of the present invention include conventional sterilization processes not requiring exposure of the interior contents of package 5 to moisture, such as Co 60 irradiation, and the like. Conventional sterilization processes such as ethylene oxide or autoclaving may be used if the suture anchors and sutures are non-absorbable.

The folder packages 5 of the present invention are preferably constructed from any material having the required structural characteristics such that the material can be readily die cut, and scored. In addition, the material must be easily folded and sterilizable. The materials include those known in the art for packaging sutures and medical devices, including paper, plastic, foils, and laminates of one or more thereof. However, it is particularly preferred in the practice of the present invention to utilize a heavyweight, relatively stiff, medical grade paper or paperboard such as 0.007 –0.016" suture board.

The advantages of the packages of the present art are numerous. The package 5 of the present invention has many advantages. It is easy to manufacture out of conventional materials. The package 5 is extremely easy to assemble. Other advantages include protection of the contents of the package 5 from damage and shifting during shipping, handling, sterilization and storage. In addition, the suture anchor assembly 205 and applicator 240 are easily removed by medical professional in the operating room without damage.

Although this invention has been shown and described with respect to detailed embodiments thereof, it will be understood by those skilled in the art that various changes of form and detail thereof may be made without departing from the spirit and scope of the present invention.

I claim:

1. A foldable package for a suture anchor, the package comprising;

a base panel, said base panel having opposed first and second major sides and opposed first and second minor sides;

a connecting panel having opposed first and second major sides and opposed first and second minor sides, said connecting panel foldably connected along a first side to the second major side of the base panel;

a cover panel having first and second major sides and opposed first and second minor sides, wherein the first major side of the cover panel is foldably connected to the second major side of the connecting panel;

a first end panel foldably connected to a first minor side of the cover panel;

a second end panel foldably connected to the second minor end of the cover panel;

means for retaining a suture anchor assembly mounted to the base panel, comprising a foam member having a semi-circular cut-out;

means for locking the cover panel to the base panel, comprising at least one tab pocket;

means for locking the end panels to the cover panel, comprising a tab extending from the end panel, and a tab pocket in the cover panel for receiving the tab;

a first connecting panel foldably mounted between the cover panel and the first end panel, and a second connecting panel foldably mounted between the cover panel and the second end connecting panel;

L-shaped tab members in the base panel for retaining the shaft of a suture anchor applicator; and, a handle cover panel foldably mounted to the base panel;

wherein the connecting panel is substantially perpendicular to both the base panel and the cover panel when the package is assembled.

2. The package of claim 1 further comprising a suture anchor assembly and a suture anchor applicator.

3. The combination of a foldable package and a suture anchor and applicator assembly, the combination comprising;

a base panel, said base panel having opposed first and second major sides and opposed first and second minor sides;

a connecting panel having opposed first and second major sides and opposed first and second minor sides, said connecting panel foldably connected along a first side to the second major side of the base panel;

a cover panel having first and second major sides and opposed first and second minor sides, wherein the first major side of the cover panel is foldably connected to the second major side of the connecting panel;

a first end panel foldably connected to a first minor side of the cover panel;

a second end panel foldably connected to the second minor end of the cover panel;

means for retaining a suture anchor assembly mounted to the base panel, comprising a foam member having a semi-circular cut-out;

means for locking the cover panel to the base panel, comprising at least one tab pocket;

means for locking the end panels to the cover panel, comprising a tab extending from the end panel, and a tab pocket in the cover panel for receiving the tab;

a first connecting panel foldably mounted between the cover panel and the first end panel, and a second connecting panel foldably mounted between the cover panel and the second end connecting panel;

L-shaped tab members in the base panel for retaining the shaft of a suture anchor applicator; and, a handle cover panel foldably mounted to the base panel;

wherein the connecting panel is substantially perpendicular to both the base panel and the cover panel when the package is assembled; and, a suture anchor and suture anchor applicator mounted to the base panel such that the anchor is maintained within the semi-circular cut-out of the foam member.

* * * * *

UNITED STATES PATENT AND TRADEMARK OFFICE
CERTIFICATE OF CORRECTION

PATENT NO. : 5,788,063
DATED : August 4, 1998
INVENTOR(S) : William Van Ness It is certified that error appears in the above-indentified patent and that said Letters Patent is hereby corrected as shown below:

On the Title Page, Item [57] Abstract, line 17, "form" should be ---- from ----.

Signed and Sealed this

Third Day of April, 2001

Attest:

NICHOLAS P. GODICI

Attesting Officer     Acting Director of the United States Patent and Trademark Office